United States Patent
Woods et al.

(10) Patent No.: US 7,052,912 B1
(45) Date of Patent: May 30, 2006

(54) METHODS AND APPARATUS FOR THE MICRO- AND MACROPROPAGATION OF REED GRASSES

(76) Inventors: Susan H. Woods, 520 Old Riceville Rd., Athens, TN (US) 37303; John E. Woods, 520 Old Riceville Rd., Athens, TN (US) 37303

( * ) Notice: Subject to any disclaimer, the term of this patent is extended or adjusted under 35 U.S.C. 154(b) by 146 days.

(21) Appl. No.: 10/035,215

(22) Filed: Jan. 4, 2002

Related U.S. Application Data

(60) Provisional application No. 60/259,719, filed on Jan. 4, 2001.

(51) Int. Cl.
*C12N 5/00* (2006.01)
*C12N 5/02* (2006.01)

(52) U.S. Cl. ............... 435/430.1; 435/420; 435/430

(58) Field of Classification Search ........... 435/430.1, 435/430, 420; 47/58, 59 R, 62 R, 62 E, 47/62 N, 63, 59 S, 18
See application file for complete search history.

(56) References Cited

U.S. PATENT DOCUMENTS

| | | | | |
|---|---|---|---|---|
| 4,607,454 | A * | 8/1986 | Koike ........................... | 47/63 |
| 4,818,693 | A * | 4/1989 | Stuart et al. ............... | 435/430.1 |
| 5,334,530 | A * | 8/1994 | Woods et al. ............... | 435/430.1 |
| 5,561,943 | A * | 10/1996 | Valstar ........................ | 47/39 |
| 6,821,782 | B1 * | 11/2004 | Marton et al. ............... | 435/430 |
| 2002/0166149 | A1 * | 11/2002 | Marton et al. ............... | 800/320 |
| 2002/0174455 | A1 * | 11/2002 | Marton et al. ............... | 800/295 |

FOREIGN PATENT DOCUMENTS

WO    WO 02063023 A2 *  8/2002

OTHER PUBLICATIONS

Linder, Cecelia C. and John L. Gallagher Tissue Culture and regeneration of the giant reed, Arundo donax L. 1998 Annual Meeting of the Botanical Society of America Aug. 2-6, 1998 Baltimore, MD Am. J. Botany 85(6): p. 89 Jun. 1998.*

Ellen G. Sutter "General Laboratory Requirements, Media and Sterilization Methods" IN R. N. Trigiano and D. J. Gray, eds. Plant Tissue Culture Concepts and Laboratory Exercises 1996 CRC Press, Inc. pp. 12-25.*

(Continued)

*Primary Examiner*—Anne Marie Grunberg
*Assistant Examiner*—W. C. Haas
(74) *Attorney, Agent, or Firm*—M. Elisa Lane; Raymond H. J. Powell

(57) ABSTRACT

The present invention provides methods for the micropropagation of reed grasses, particularly *Arundo donax*. In addition, the present invention provides methods for the macropropagation of bamboo and reed grasses, which utilize a unique float bed system and apparatus. The advantages of the present invention are that desirable plant clones can be obtained for planting in plantations and the methods are much more cost and labor efficient than traditional propagation techniques.

29 Claims, 2 Drawing Sheets

OTHER PUBLICATIONS

James D. Caponetti et al. "History of plant tissue and cell culture" IN R. N. Trigiano and D. J. Gray, eds. Plant Tissue Culture Concepts and Laboratory Exercises 1996 CRC Press, Inc. pp. 3-8.*

Murashige, T. and Skoog, F. "A Revised Medium for Rapid Growth and Bio Assays with Tobacco Tissue Cultures" Physiologia Plantarum, vol. 15, 1962 pp. 473-497.* http://www.bioproducts-bioenergy.gov/pdfs/bcota/abstracts/8/76.pdf☐☐Woods et al. New Developments in the Giant Reed (Arundo donax) and Bamboo Two Highly Productive Biomass Crops for Food, Fuel and Fiber. Undated.* http://plant-tc.coafes.umn.edu/listserv/1999/log9909/msg00311.html☐☐Boslea, Michael Arundo Donax (What is PAA?).* http://plant-tc,coafes.umn.edu/listserv/1999/log9909/msg00236.html☐☐Dr. John E. Woods TC Protocols for Arundo donax.* http://plant-tc.coafes.umn.edu/listserv/1999/log9909/msg00266.html☐☐Dr. John E. Woods Re: TC Protocols for Arundo donax.* http://plant-tc.coafes.umn.edu/listserv/1999/log9910/msg00105.html☐☐Petr Schwott Re: TC protocols for Arundo donax.*

Szilard Toth and Gunda Mix-Wagner "Embryogenic callus induction of different explants of Miscanthus sinensis, Miscanthus x giganteius and Arundo donax genotypes" Sustainable Agriculture for Food, Energy and Industry pp. 249-253 1998 James & James Ltd.*

* cited by examiner

Figure 2
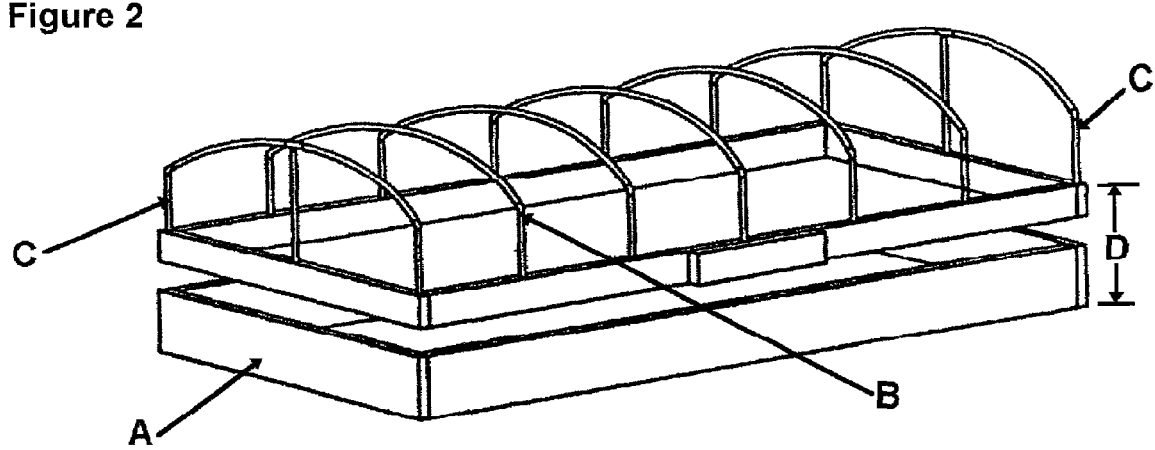
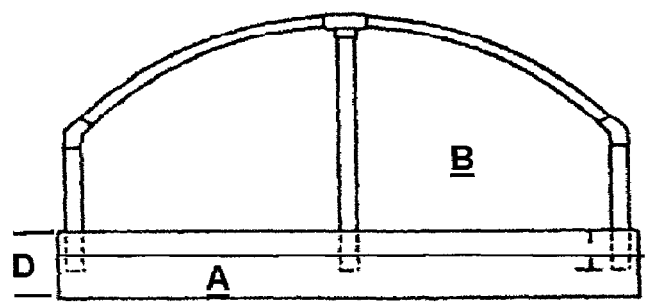
Figure 3

METHODS AND APPARATUS FOR THE MICRO- AND MACROPROPAGATION OF REED GRASSES

This application claims priority of provisional application, U.S. Ser. No. 60/259,719, filed Jan. 4, 2001.

FIELD OF THE INVENTION

The present invention provides methods for the micropropagation of reed grasses, particularly *Arundo donax*. In addition, the present invention provides methods for the macropropagation of bamboo and reed grasses, which utilize a unique float bed system and apparatus.

BACKGROUND OF THE INVENTION

Giant Reed Grass, or *Arundo donax*, and bamboos have long been recognized as important non-wood industrial biomass-producing plants that can be grown on a wide variety of soil types and in a wide range of climatic conditions. *Arundo donax* is a perennial member of the grass family and has an appearance somewhat like bamboo or sugar cane. *Arundo donax* reaches maturity in about a year, can be harvested annually, and produces usable fiber at a rate of more than twenty-five times that of timber. Over 20,000 plants can be grown in a standard acre of land (approximately 208 feet long by 208 feet wide). Arundo is extremely hardy, has few natural enemies, and grows in poor soils without fertilizer and very little rainfall. The plant flourishes in warm climates and is a very efficient converter of the sun's radiation into biomass. Once established, Arundo grows like bamboo—spreading its roots and producing a number of new shoots. Mature stalks grow to an average height of twenty-five feet and an average diameter of one inch. Arundo stalks can be processed and chipped at the harvest site, and are amenable to storage due to a natural waxy coating on the stalks. Fifty thousand hectares of Arundo produces as much usable fiber as 1,250,000 acres of trees.

Arundo can be processed into particles to make paper products and particle boards by methods known in the art. See, for instance, WO 99/66119, which is incorporated herein in its entirety by reference. In addition, both Arundo and bamboo can be used to generate heat and make fuel such as ethanol, as well as for food, phytoremediation, and carbon sequestration.

Bamboo, on the other hand, is one of the most universally useful plant commodities known. Bamboo provides food, raw material, shelter and even medicine for the greater part of the world's population. The fibers of bamboo are long, thin and of high quality. They are many times better and stronger than wood fiber. With good physical and mechanical properties, and low shrinkage, they are ideal for many industrial applications. They can be used, inter alia, to make particleboard and oriented-strand board. They are an excellent source of fiber for making paper pulp. Like Arundo, bamboo can be burned to generate heat and make fuels such as ethanol.

The major factor that has limited Giant Reed Grass and bamboo utilization has been the cost of planting and availability of planting material when attempting to establish large plantations. Before the development of the present invention, plants for plantation establishment were usually dug and moved by intensive manual labor. This also required a large stock of wild planting material to be available near the desired plantation site and also locally available, low-cost labor. Very few plantations have ever been established due to these restrictions, even though the commercial potential of these plants was well known since the early 1900's. In essence, this invention solves the major problems restricting the use of these plants as a large-scale feedstock for the industrial production of, as examples, paper pulp, fuel, and food and building materials.

The availability of these non-wood fiber resources provided by the present invention has a tremendous impact on the wood fiber situation worldwide. The present invention provides for the first time methods of successful plant culture and plant regeneration via somatic embryogenesis utilizing vegetative explants from Arundo donax plant parts. In addition, the present invention provides for the first time methods for the non-aseptic mass macropropagation of bamboo and Arundo, which reduces labor requirements and overcomes a lack of plant stock material at the industrial site. Thus, the present invention succeeds in eliminating major barriers restricting large-scale biomass plantation establishment of bamboo and Arundo. In the case of Arundo, for instance, 22 million plants, enough to plant 18,000 acres, can be produced and planted efficiently in one year with the present invention, requiring 113 laboratory, nursery, and plantation workers working forty hours per week. With conventional propagation systems, a labor force of 5,023 people working 365 days might be able to accomplish this if the plant stocks for vegetative division were available. The plant stocks required would be about 6 thousand acres in size. No known stocks of this size are currently available in the United States.

SUMMARY OF THE INVENTION

An object of the present invention is to provide methods for the aseptic in vitro propagation of *Arundo donax* by inducing somatic embryogenesis from vegetative and floral explants from *Arundo donax* plants. Briefly, explants are cultured on embryo initiation medium to induce somatic embryogenesis. The somatic embryos can either be multiplied in liquid suspension culture or germinated to produce plantlets. These plantlets can be used to provide explant material for somatic embryogenesis or multiplied in a shoot multiplication system. Multiple propagation pathways in this aspect of the present invention ensure a continuous supply of plants in the event of a problem in one pathway. This system also ensures obtaining plantlets of uniform quality, both phenotypically and genetically.

Another object of the present invention is to provide for the macropropagation under non-septic conditions of bamboo and *Arundo donax*. In this aspect of the invention, plantlets are introduced to a float bed nursery system, in which they are fed along the length of the float bed in a continuous, "conveyor belt" type fashion, during which time they develop into mature plants ready for transplantation into the field. This macropropagation system has several advantages over conventional propagation methods. Primary labor requirements are reduced significantly, including the elimination of the labor-intensive tasks weeding and of pulling plants from a plant bed for further propagation. Also, the risk of a plant bed failure from dry conditions or watering system failures in the field is eliminated. Further, the daily transplantation rate is increased, since plants produced by this system can be transplanted any time of day. The storage of unused plants is simply a matter of re-floating the trays. Moreover, the survival rate of field transplants from this system is greatly increased due to less root disturbance as compared to conventional methods. In this float bed system, the character and constituents of the aqueous medium in which the plantlets are floating can be more efficiently tested and regulated as opposed to conventional methods.

In one embodiment of this aspect of the present invention, once a tray of plantlets is mature enough to be topped by clipping and replanting in the float bed, then no further plantlets may be required from the in vitro system described above. In another embodiment of this aspect of the invention, the continuous supply of plants from the float bed can be transplanted with a mechanical transplanter, which greatly reduces the cost of establishing a plantation.

Especially, by combining the above two micro- and macropropagation methods, for the first time there is allowed the economical development of large sustainable plantations of the most productive biomass plants ever reported.

The plantlets and plants obtained by the methods of micro- and macropropagation, respectively, are also contemplated as being part of the present invention, inasmuch as they are of a unique quality and of an elite plant selection, as well as clonal in nature.

In a third aspect of the present invention is an apparatus, which is a continuous float bed nursery for the propagation of plants. This apparatus is particularly suited for Arundo and bamboo, although other plants may also be grown in this apparatus, the only limiting factor being their susceptibility to being waterlogged. Briefly, the float bed apparatus comprises a bottom frame structure of about six inches high, which is constructed on a level smooth base to form a device to hold a liquid medium at a depth of about four to six inches, onto which a canopy framework of a sufficient height to accommodate the plants is attached to or lays upon the bottom frame. Floatable trays containing plantlets are introduced to the bottom frame structure containing the aqueous medium at one end and floated along the length of the apparatus such that when they reach the other end, the plants are mature enough to be transplanted into the field. This apparatus is different from conventional float beds in that this system does not require an enclosed greenhouse, nor do conventional float beds have shading or misting systems.

Further objects and advantages of the present invention will become apparent from a consideration of the drawings and ensuing description.

BRIEF DESCRIPTION OF THE DRAWINGS

These and various other features and aspects of the present invention will be readily understood with reference to the following detailed description taken in conjunction with the accompanying drawings, in which like or similar numbers are used through-out, and in which:

FIG. 2 is a perspective drawing of a float bed apparatus of the present invention, showing the bottom frame (A) and the canopy frame (B). The ends are depicted as (C). The desired liquid medium depth will determine the sidewall (D) height.

FIG. 3 is a detail of the end view of the float bed canopy frame cover (B), which attaches directly to or sits on the bottom frame (A) of FIG. 2.

DETAILED DESCRIPTION OF THE PREFERRED EMBODIMENTS

Figure 1:
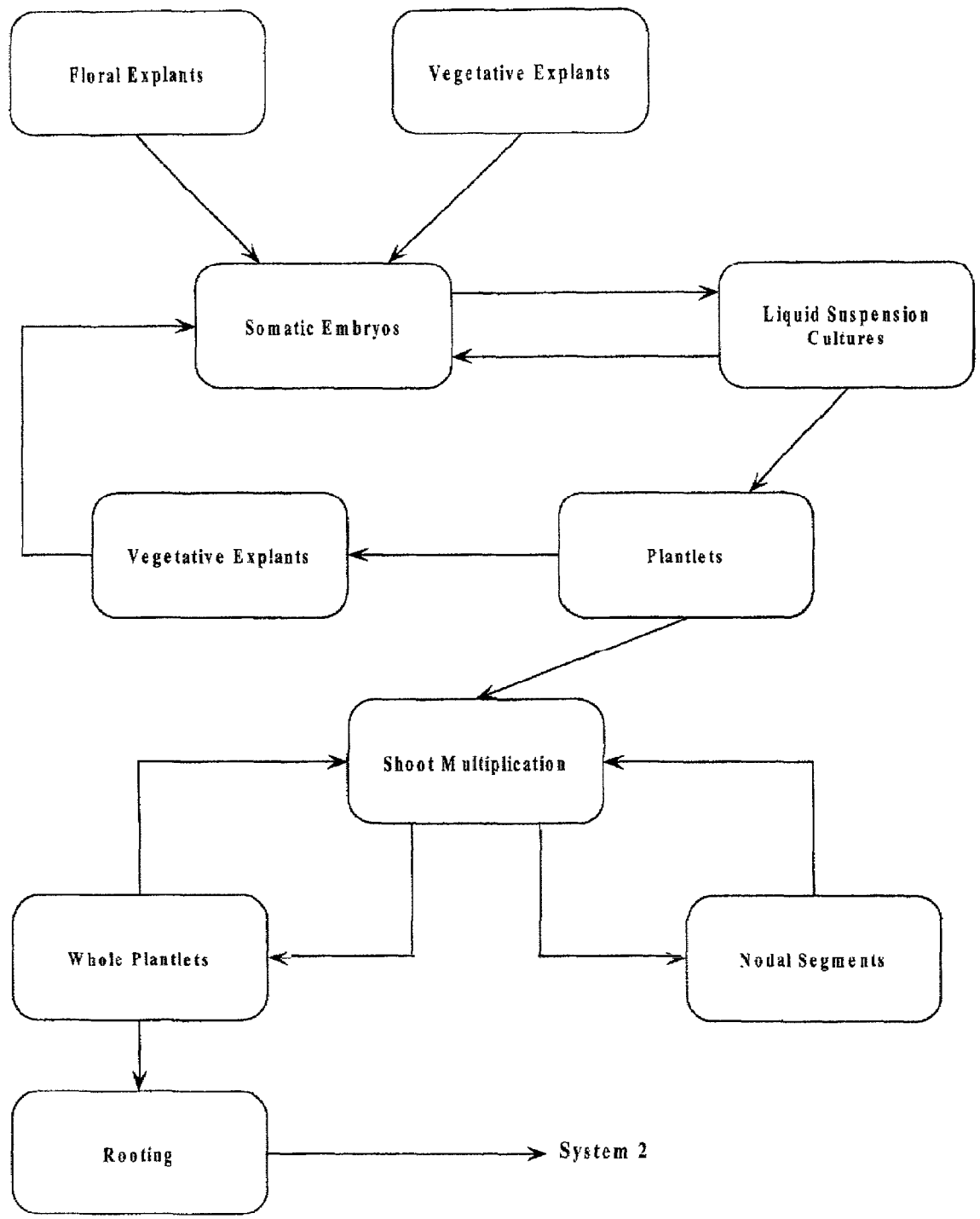
FIG. 1 is a diagram showing the multiple micropropagation pathways for *Arundo donax* according to, and which are encompassed by, the present invention.

The present invention is directed, in general, to the mass propagation of non-wood, industrial biomass-producing plants, most notably *Arundo donax* and the Bamboos. The invention utilizes methods and an apparatus whereby a continuous supply of high quality plants can be produced in a time- and cost-efficient manner.

Micropropagation

In a first aspect of the present invention, a method is provided for the micropropagation in tissue culture of plantlets of *Arundo donax*. This method involves obtaining explant material from meristematic tissue, or juvenile or immature Arundo donax plant structures, cleaning it to obtain aseptic explant material, introducing this clean material into a semi-solid or solid embryo induction medium, which allows for the production of mature embryos, and culturing the mature embryos on semi-solid germination medium to thereby generate multiple plantlets. In other words, this method provides for the somatic embryogenesis of *Arundo donax*, which has not been previously accomplished. By "somatic embryogenesis" is meant a process of embryo initiation and development from vegetative or non-gametic cells. The embryos from a given tissue source are presumed to be genetically identical.

By "explant material" is meant a piece of plant tissue taken from a donor plant for culturing. Examples of explant materials include immature floral parts, meristematic tissue, leaf, leaf sheath, axillary branches, roots and rhizomes, nodes and nodal buds, which are obtained by methods known in the art. By "meristematic tissue" is meant a group of tissue forming cells capable of further development into plant organs. Preferably, the explant material is floral parts. Most preferably, the explant tissue is immature floral parts. By "floral parts" is meant (immature) flowering material that is taken from a flowering shoot just as the floral material begins to emerge from the leaf sheaths. Explant material may be taken in a series from the base of the floral shoot where the reproductive structures are still largely undifferentiated to the upper portion of the shoot where immature reproductive structures (ovules and anthers) are visible.

In a preferred embodiment of the invention, the explant material is chosen from "elite" plants, i.e. plant chosen for desirable phenotypic and genetic characteristics. The end-product plants will be of a uniform quality, which can be regenerated and propagated as the parent plants through the system.

As in any tissue culture system, aseptic conditions are required. As such, the explant material must be cleaned in order to remove any undesirable surface microbes. To accomplish this, the explant material is cleaned by washing with any of various antimicrobial, or antiseptic, solutions. An example thereof is a sterile aqueous solution of alcohol, sodium hypochlorite and a surfactant, in combination or in a series of washes with each solution.

The cleaned explant material is placed onto a semi-solid embryo induction medium, which contains appropriate plant growth hormones for embryo induction. This embryo induction medium will contain a basal plant tissue culture medium, such as standard commercially available media, which would include preparations as described by Linsmaier and Skoog (LS medium, LINSMAIER, E. M. and F. SKOOG: Physiol. Plant., 18, 100–127, (1965)) and Murashige and Skoog (MS medium, MURASHIGE, T. and F. SKOOG, Physiol. Plant., 15:473–497 (1962)). See Table 1. LS medium, or MS medium supplemented with Gamborg's vitamins (see Table 2), are preferred embodiments. To the basal medium are added components that will facilitate embryogenesis and shoot multiplication. In particular, one or more cytokinins are added to the basal medium; examples include: 6-furfurylaminopurine ("kinetin") at 1–3 mg/l; 6, benzylaminopurine ("BA") at 0.5–2 mg/l; indoleacetic acid ("IAA") at 1–3 mg/l, 2,4-dichlorophenoxyecetic acid ("2,4-D") at 1–6 mg/l and thidiazuron ("TDZ") at 0.05–1.0 mg/l. A carbohydrate source is added to the media, which is preferably a sugar such as sucrose, at 20–50 grams per liter. In addition to the nutrients of the medium, there should be a gelling substance to make it a solid or semi-solid substrate. Commonly used is a substance such as agar, or its derivatives, or in a preferred embodiment is Gelrite® (Merck & Co., Inc. (Rahway, N.J.), Kelco Division, USA) or its equivalent. Gelrite® is a harder medium than agar, and thus has lower water potential (holding power), allowing for easier access of the plant culture to the aqueous nutrient solution. All micropropagation media, including all additional components, is adjusted to a pH of from about 5.0 to about 6.0 and sterilized by, for instance, autoclaving at about 120° C. for about 30 minutes prior to use.

To the basal medium are added components that will facilitate embryogenesis and shoot multiplication. In particular, one or more cytokinins are added to the basal medium; examples include: 6-furfurylaminopurine ("kinetin" or "K") at 1–3 mg/L; 6, benzylaminopurine ("BA") at 0.5–2 mg/L; indoleacetic acid ("IAA") at 1–3 mg/L, 2,4-dichlorophenoxyecetic acid ("2,4-D") at 1–6 mg/L and thidiazuron ("TDZ") at 0.05–1.0 mg/L. A carbon source, preferably sucrose, at about 20–50 grams per liter is required. As a preferred embodiment for embryogenesis is a medium containing MS basal salts supplemented with LS vitamins, IAA (1.0 mg/L), 2,4-D (2 mg/L) and sucrose (20 g/L). A preferred embodiment for shoot multiplication is a medium containing MS basal salts, Gamborg's vitamins, BA (1.0 mg/L), TDZ (0.05 mg/L) and sucrose (30 g/L), although minor variations of constituents in the formulation are contemplated as part of the present invention.

TABLE 1

Murashige & Skoog Salt Base*

| Components | mg/liter |
|---|---|
| $NH_4NO_3$ | 1650.000 |
| $KNO_3$ | 1900.000 |
| $CaCl_2$ (Anhydrous) | 333.000 |
| $KH_2PO_4$ | 181.000 |
| $MgSO_4$ (Anhydrous) | 170.000 |
| FeNaEDTA | 36.700 |
| $H_3BO_3$ | 6.200 |
| $MnSO_4.H_2O$ | 16.900 |
| $ZnSO_4.7H_2O$ | 8.600 |
| KI | 0.830 |
| $Na_2MoO_4.2H_2O$ | .250 |
| $CuSO_4.5H_2O$ | .025 |
| $CoCl_2.6H_2O$ | .025 |
| TOTAL | 4303.530 |

*LS medium is MS Salt Base with 100 mg/L i-Inositol and 0.4 mg/L Thiamine HCl.

TABLE 2

Gamborg's Vitamins

| Component | mg/liter |
|---|---|
| i-Inositol | 100.000 |
| Nicotinic acid | 1.000 |
| Pyridoxine HCl | 1.000 |
| Thiamine HCl | 10.000 |

A carbohydrate source is added to the media, which is preferably a sugar such as sucrose, at 20–50 grams per liter. In addition to the nutrients of the medium, there should be a gelling substance to make it a solid or semi-solid substrate. Commonly used is a substance such as agar, or its derivatives, or in a preferred embodiment is Gelrite® (Merck & Co., Inc. (Rahway, N.J.), Kelco Division, USA) or its equivalent. Gelrite® is a harder medium than agar, and thus has lower water potential (holding power), allowing for easier access of the plant culture to the aqueous nutrient solution.

The mature embryos can be directed through one of two pathways. In one aspect (1), clumps of about three to ten of the mature embryos are transferred onto and cultured on a semi-solid or solid germination medium to thereby generate multiple plantlets. By "plantlet" is meant a plant asexually reproduced by tissue culture. The semi-solid or solid germination medium is a basal medium as described above, supplemented with only sucrose (20–30 g/L, preferably 20 g/L) and a gelling agent (the gelling agent being one as described above). In another aspect (2), the mature embryo clumps can be divided into smaller clumps of three embryos or less, and transferred into a fresh liquid suspension culture medium comprising embryo initiation media (as described above) minus the gelling agent and with or without the addition of asparagine (preferably at 0.75 g/L) (i.e., "split" the embryo cultures), thereby allowing for further multiplication of the embryos. At one to two week intervals, the embryo clumps in these cultures can either be placed onto the germination medium as described above, or yet again subcultured (or "split") for even further multiplication.

The plantlets ultimately derived by the above methods, which contain at least root initials, can be directly planted into the soil-less media of second aspect of the present invention, described below, with or without first putting them in rooting medium. Rooting medium is a basal plant medium (for instance LS or MS), which is at one half its concentration and is supplemented with sucrose and a gelling agent. Alternatively, the plantlets can be directed into one of two pathways: (1) the plantlets can be used as a source of clean explant material to begin the above process anew, e.g., leaf, leaf sheath, node, axillary bud and root material thereof can be used to produce more embryos on embryo induction medium; or (2) whole plantlets or nodal segments thereof can be transferred to semi-solid or liquid multiplication media for shoot multiplication. With the latter alternative, the shoots can be subcultured at four to six week intervals for an indefinite period of time. Shoot multiplication media is as described above in this application. Shoots, which have not rooted, can be transferred to rooting medium or directly to a soil-less potting mixture to serve as stock plants for the second aspect of the present invention, described below. As for the soil-less medium, these are well known in the art, and the particular formulation is not critical to the present invention. Examples of materials used in soil-less medium include sphagnum peat moss, hypnum peat, reed sedge peat, composted bark, fresh bark, composted organic wastes, perlite, and vermiculite.

The above-described micropropagation techniques supply a continuous source of stock plants for the macropropagation system detailed below. In addition, plants derived from the process of somatic embryogenesis can be utilized to provide explant material for multiple pathways of plant regeneration as indicated in the diagram of FIG. 1. Multiple propagation pathways ensure a continuous supply of plants in the event of a breakdown in one pathway. This means of mass propagation makes it possible to generate a large stock of uniform plants of (elite) *Arundo donax* clones without the necessity of seeds or large vegetative plant stocks, which has heretofore not been accomplished.

As a source of Bamboo plantlets for the second aspect of the present invention can, without limitation, be those produced by the methods disclosed in U.S. Pat. No. 5,334,530 (Woods et al.), and International Publication No. WO/00/53727 (Gielis and Woods et al.), both of which are specifically and in their entireties incorporated herein by reference.

Macropropagation

In the second aspect of the present invention, which can be used alone or in conjunction with the first aspect described above, is a method and apparatus for the macropropagation of *Arundo donax* and Bamboo plants. This method and apparatus provides for a mass production of the plants that is cost and labor efficient, while providing plants of uniform high quality. The purpose of this method and apparatus is to maximize efficient plant multiplication on site, operating in a non-aseptic environment, reducing labor requirements and overcoming a lack of plant stock material at the industrial site. In this manner the invention succeeds in eliminating the major barriers that normally restrict large-scale biomass plantation establishment. In this aspect of the invention, multiple plantlets of Bamboo or *Arundo donax*, preferably from some homogeneous source, are transplanted into floatable trays that contain a soil-less potting mixture formulated for floating on water. These trays are then fed into a float bed system, an example of which is given as a third aspect of the present invention, below. The trays of plants are moved along the float bed system at periodic intervals, preferably at a daily rate, during which time the plantlets develop into plants mature enough to be transplanted into the field for complete maturation. In an alternative embodiment, float bed modules can positioned in a series in a pathway, in which case the method would comprise placing the trays in an $N^{th}$ float bed module, placing the $N^{th}$ float bed at the end of a pathway containing N−1 float bed modules, wherein the pathway permits movement of the $N^{th}$ float bed from a first position to a second position, and allowing the $N^{th}$ float bed to move along the pathway so as to permit the $N^{th}$ float bed to arrive at the second position when the plantlets are sufficiently mature for planting proximate to the second position. This method can also be performed in a conveyor belt fashion by adding a new float bed module to the first position as the $N^{th}$ float bed module arrives at the second position.

In order for development to occur in the float bed system, certain conditions therein need to be maintained and monitored. Fertilizers, temperature, hormone and other nutrient control, as well as water chemistry can be efficiently monitored in this system. In addition, float bed covers may be used to prevent sunscald, drying and wilting when required. Humidity control of the float bed environment may be accomplished by misting equipment and/or float bed covers when appropriate.

Typically, the conditions of the float bed system of the present invention are maintenance of temperature at about 60–80° F., water with fertilizer (such as NPK with minor amounts of iron, zinc, manganese, copper boron, molybdenum and sulfur), and optionally rooting hormones (depending on the requirements of the plant or clone used). Such rooting hormones include, and are preferably, indoleacetic acid ("IAA") 1-naphthaleneacetic acid ("NAA") and indole-3-butyric acid ("IBA"). Auxins are usually used without cytokinins in the rooting stage. NM, for example, is generally used in plant culture in a concentration of between 0.1–10 mg/l, more preferably not exceeding about 3 mg/l. The particular auxin and its exact concentration will depend on the clone of *Arundo donax* or Bamboo being cultured, and these concentrations of IAA, NAA and IBA can be easily determined experimentally. The pH of the of the fluid in the float bed is about 4.5 to 7.5, preferably 6.5.

A further advantage of this macropropagation system is that at the stage where the plants contain at least one node (for instance, with *Arundo donax* at the height of about 5 inches), the tops containing the node can be clipped off, optionally treated with plant hormones, and returned to a float tray at the beginning of the float bed system to start the maturation process over. This is preferably done mechanically, or may be done by hand. This keeps the system operating without new laboratory-produced plantlets being required or at least greatly reducing the need for new laboratory plantlets. Plant growth regulators and nutrients in the water of the float bed may be added to stimulate these plantlets to root and grow to a size needed for transplantation to the field, typically about 30 days for *Arundo donax* and about three months for bamboo.

Float Bed Apparatus

In a third aspect of the present invention is the actual float bed apparatus for use in the macropropagation of the plants. The float bed comprises a frame of about six inches high, lined with a plastic film of about 6 mils thickness, and constructed on a level smooth base to form a device to hold water at a depth of about four to six inches. See FIGS. 2 and 3. FIG. 3 shows an end view of a preferred pipe frame framework with a means of attachment for the supports of the frame. A first portion of the float bed apparatus may have a shade-cloth or plastic sheet cover of appropriate light reduction characteristics and/or a misting apparatus when needed and which can be removed or exchanged as desired, which may serve to protect the introduced plantlets from wilting or drying and to acclimatize newly transplanted laboratory plantlets. A misting system is attached preferably to the peak of the support pipes (FIG. 3) with emitters spaced appropriately along the linear dimension of the float bed cover to attain the desired humidity. See, generally, FIGS. 2 and 3.

In a preferred embodiment, commercially available styrofoam plug trays of about 14×27×3 inch dimensions, available for instance from Hummert™ International, are used to contain plantlets in a soil-less potting mix, although any floating tray that accomplishes the same purposes of being floatable while allowing the infiltration of water and nutrients to the plants, many also commercially available, may be used.

The dimensions of the float bed should conform to the number of plants needed per time period, which is easily determinable. That is, the number of transplants required daily from each float bed will determine the float bed specifications of length and width. The desired water level in the float bed will determine the sidewall height. For instance, 10,000 *Arundo donax* plantlets are needed per hectare per day for planting in a plantation. These plants need to grow for about thirty days in the nursery before field planting. If each float tray holds 288 plantlets and an unusually high (five times normal) ten percent loss of plants, then thirty-nine float trays per day are needed to plant one hectare. If the float bed dimensions allow thirty-nine float trays to occupy ten linear feet of space, then a three hundred foot long float bed could produce enough plants for a one hectare per day planting. Each day all float trays are floated toward the opposite end of the float bed from which the field-ready plants are removed for transplantation into the field. Thus, in this example, thirty-nine trays are removed with field-ready transplants, and thirty-nine trays of new plantlets are added at the opposite end of the float bed, thereby allowing for the system to operate in a conveyor belt-type fashion.

A means to control the water (or liquid medium) level in the float bed system may be present in the apparatus. With such a device the float bed fluid levels can be regulated for optimum operation. Thus, the invention can be used in an ebb and flow manner, if desired, which is a cost effective method to water large numbers of small plants. By "ebb and flow" is meant system that periodically floods the potted plants; for example, the water level in the bed is filled with fluid (such as water and fertilizers) to saturate the potted plants, and then drained once or twice a day.

As mentioned previously, at about 22–26 days in the float bed system, *Arundo donax* plantlets may be clipped (height approximately 5 inches) and then vacuumed in a bag or by hand, sorted and treated with hormones, if desired, and replanted in new float trays to begin the process anew.

The present invention is further described by the following, non-limiting, examples.

EXAMPLE 1

*Arundo donax* Somatic Embryogenesis and Plant Regeneration

Plant Material Flowering shoots of *Arundo donax* were obtained from four clones (designated A, B, C, D) maintained in experimental plots at Auburn University. Two stages of flowering material were used: 1. Floral material three-fourths extruded from the leaf sheath, designated old (O). 2. Floral head still 99% enclosed in leaf sheath, designated young (Y). A shoot from each of the two stages was divided into three sections: 1. bottom (B) 2. middle (M) 3. upper (U). Plant material was washed in soapy water, rinsed under running water for 10 minutes, washed with agitation in 20% Clorox for 20 minutes and rinsed five times in sterile water.

Methods Media used were Linsmaier and Skoog basal medium supplemented with 2, 4-D, and either IAA, K, or BA, for embryo generation and for the germination Murashige and Skoog basal medium. All media were adjusted to pH 5.8, gelled with 0.2% Gelrite, and autoclaved for 25 min at 120° C.

Explants of about 2–5 mm in length were taken from all samples of washed material (bottom, middle and upper of both young and old shoots) and were plated 20 explants per plate. There were four replicates of each sample with half of the plates cultured in light and half cultured in dark for a total of 288 plates.

Cultures were scored and subcultured at 30 day intervals for at least four passages. Cultures were scored on callus size, embryo production and embryo germination. For evaluation of plant regeneration, three clumps of embryos, 4–10 mm in diameter, were cultured per plate on germination medium (MS basal medium with no supplements).

Results Material from all samples showed some response. The samples producing the most embryos came from the upper portion of the young material of Clone C that was cultured in the light on the LS medium supplemented 2 mg/L 2,4-D and 1 mg/L IAA.

EXAMPLE 2

Plant Material Explant pieces 1–5 mm. in length were excised from sterile plantlets produced from embryogenic cultures. Portions of leaf, leaf sheath, nodes, and roots were cultured in the same manner as in Example 1., using the preferred medium. All explant sources were responsive to some degree, but the preferred explant material was from the leaf sheath, which produced embryos and plantlets as in Example 1.

EXAMPLE 3

Embryo multiplication in suspension culture. Five embryo clusters of 5–15 embryos each were visually selected from cultures described in Example 1. and transferred to Erlenmeyer flasks containing a liquid medium. The medium utilized was the preferred medium for embryogenesis given in Example 1., minus the gelling agent and with or without the addition of asparagine (0.75 g/L). Embryo clusters were divided on a weekly basis with half of the embryo clusters returned to fresh liquid medium and half the embryo clusters placed on germination medium to germinate into plantlets.

EXAMPLE 4

Shoot multiplication Plants 2–4 cm. in height selected from germinated embryos described in Example 1. Were cultured in 100 ml. culture vessels containing 30 ml of semi-solid medium. The preferred medium was MS basal salts supplemented with Gamborg's vitamins, BA (1.0 mg/l), TDZ (0.05 mg/l) and sucrose (30 g/l). Cultures were divided on a monthly basis. Clusters of shoots were divided into smaller divisions of at least three shoots per cluster and placed on either fresh multiplication medium for continued multiplication or on rooting medium. Plants can be rooted on half strength MS medium or planted directly to a soilless medium in the greenhouse.

Although presently preferred embodiments of the present invention have been described in detail herein, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A method for the propagation of *Arundo donax*, comprising:
    (a) obtaining explant material from meristematic tissue, juvenile or immature *Arundo donax* plant structures;
    (b) cleaning said explant material to obtain aseptic plant material;
    (c) introducing said aseptic explant material into a semi-solid or solid embryo induction medium, allowing for the production of mature embryos;
    (d) culturing the mature embryos on semi-solid or solid germination medium to thereby generate plantlets;
    (e) transferring plantlets generated from step (d) to trays which will float on a liquid medium in a float bed nursery apparatus in a non-aseptic manner and which float bed nursery provides conditions conducive to growth and multiplication of the plantlets, and placing said trays at one end of said apparatus; and
    (f) moving the trays of plantlets along a length of the float bed apparatus at a periodic interval, such that when the trays reach the opposite end of the apparatus the plantlets have multiplied and grown sufficiently to reach a maturity of plants that are ready to be planted in the field, whereby a plurality of *Arundo donax* plants is obtained.

2. The method of claim 1, further comprising transferring the mature embryos from step (c) to a liquid suspension culture medium to thereby induce the production of more embryos prior to step (d).

3. The method of claim 2, further comprising splitting and subculturing the resultant multiple embryos in fresh liquid suspension medium to induce further embryo multiplication, prior to step (d).

4. The method of claim 1, wherein the embryo induction medium comprises LS or MS medium supplemented with sucrose, a gelling agent, and one or more of 2,4-dichlorophenoxyacetic acid (2,4-D), 6-benzyladenine (BA), indoleacetic acid (IAA), kinetin (K), and thidiazuron (TDZ).

5. The method of claim 4, wherein the embryo induction medium comprises LS medium supplemented with IAA, 2,4-D and sucrose.

6. The method of claim 5, wherein the LS medium comprises 1.0 mg/L IAA, 2 mg/L 2,4-D and 20 g/L sucrose.

7. The method of claim 1, wherein the germination medium comprises LS or MS medium supplemented with sucrose and a gelling agent.

8. The method of claim 2, wherein the liquid suspension culture medium comprises LS or MS medium supplemented with sucrose, and one or more of 2,4-dichlorophenoxyacetic acid (2,4-D), 6-benzyladenine (BA), indoleacetic acid (IAA), kinetin (K), and thidiazuron (TDZ).

9. The method of claim 8, wherein the liquid suspension culture medium comprises one or more of 1–6 mg/L 2,4-D, 0.5–2 mg/L BA, 1–3 mg/L K, and 0.05–1.0 mg/L TDZ.

10. The method of claim 8, wherein the liquid suspension culture medium further comprises asparagine.

11. The method of claim 1, wherein the plantlets are allowed to grow and multiply in the float bed apparatus for about 30 days to reach such maturity of plants that are ready to be planted in the field.

12. The method of claim 1, wherein additional plantlets for transferring to trays are generated between steps (d) and (e) by transferring plantlets or nodal segments thereof from step (d) to a solid or semi-solid shoot multiplication medium to obtain multiple shoots from the plantlets.

13. The method of claim 1, further comprising obtaining plant material from maturing plantlets in the float bed and returning the plant material to a float tray to start the multiplication and growth of plantlets anew in the float bed apparatus, thereby reducing or eliminating the need for plantlets obtained from steps (a) through (d).

14. The method of claim 13, wherein said plant material is obtained from maturing plantlets in the float bed apparatus at a stage where the plantlets, whereby the tops each comprise at least one node, and whereby the plant material is obtained by clipping off the tops of the maturing plants containing the at least one node.

15. The method of claim 13, wherein the plant material is obtained from plantlets at about the 22nd to the 26th day in the float bed apparatus.

16. The method of claim 14, wherein the tops containing at least one node are treated with plant hormones when introduced anew to the float bed apparatus.

17. The method of claim 1, wherein new trays of plantlets are added to the float bed apparatus when trays with mature plants are removed at the opposite end, thereby operating the apparatus in a continuous, conveyor belt fashion.

18. The method of claim 1, wherein the periodic interval is daily.

19. The method of claim 1, wherein the propagation of plants is conducted in the float bed apparatus which further comprises a bottom frame structure of about six inches high, which is constructed on a level smooth base to form a device to hold a liquid medium at a depth of about four to six inches, and onto which a canopy framework of a sufficient height to accommodate the plants is attached to the bottom frame.

20. The method of claim 19, wherein the propagation of plant is conducted in the float bed apparatus and wherein the bottom frame structure is lined with a plastic film of about 6 mils thickness to retain the liquid medium in the float bed.

21. The method of claim 19, wherein the propagation of plants is conducted in the float bed apparatus and wherein the canopy framework is constructed of plastic pipe.

22. The method of claim 19, wherein the propagation of plants is conducted in the float bed apparatus and wherein at least a portion of one end of the canopy framework under which plantlets are transferred to the float bed apparatus is covered with a material having sufficient light reduction characteristics to allow growth but to protect plantlets from wilting and to acclimatize newly transplanted plantlets.

23. The method of claim 19, wherein the propagation of plants is conducted in the float bed apparatus and which further comprises an overhead misting apparatus with emitters spaced along the linear dimension of the canopy framework to attain desired humidity.

24. The method of claim 19, wherein the propagation of plants is conducted in the float bed apparatus and wherein the bottom frame structure contains water that is supplemented with nutrients and plant hormones conducive to plant growth and multiplication.

25. A method for the propagation of *Arundo donax* to obtain plants thereof, comprising:
 (a) obtaining plantlets of the *Arundo donax* by somatic embryogenesis or from portions of mature plants wherein the portion obtained contains at least one node;
 (b) transferring said plantlets or nodal material to trays which will float on a liquid medium in an $N^{th}$ float bed module that provides conditions conducive for growth and multiplication of the plantlets or nodal material;
 (c) placing the $N^{th}$ float bed module at the end of a pathway containing N–1 float bed modules, said pathway permitting movement of the $N^{th}$ float bed from a first position to a second position; and
 (d) permitting the $N^{th}$ float bed module to move along the pathway so as to permit the $N^{th}$ float bed module to arrive at the second position when the plantlets are sufficiently mature for planting.

26. The method of claim 25, for the propagation of *Arundo donax*, wherein the $N^{th}$ float bed is transported from the second position to the first position for introduction of a new tray of plantlets when the tray with mature plants is removed at the second position, thereby permitting the apparatus to operate in a continuous, conveyor belt fashion.

27. The method of claim 12, wherein the shoot multiplication medium comprises LS or MS medium supplemented with sucrose, a gelling agent, and one or more of 2,4-dichlorophenoxyacetic acid (2,4-D), 6-benzyladenine (BA), indoleacetic acid (IAA), kinetin (K), and thidiazuron (TDZ).

28. The method of claim 27, wherein the shoot multiplication medium comprises MS medium supplemented with Gamborg's vitamins, BA, TDZ and sucrose.

29. The method of claim 28, wherein the MS medium comprises 1.0 mg/L BA, 0.05 mg/L TDZ and 30 g/L sucrose.

* * * * *